United States Patent [19]

Scrima

[11] Patent Number: 5,210,118

[45] Date of Patent: May 11, 1993

[54] METHOD FOR STABILIZING SYNTHETIC THERMOPLASTIC MATERIALS AGAINST THERMAL DEGRADATION

[75] Inventor: Roberto Scrima, Bologna, Italy

[73] Assignee: Ciba-Geigy Corporation, Ardsley, N.Y.

[21] Appl. No.: 712,849

[22] Filed: Jun. 10, 1991

[30] Foreign Application Priority Data

Jun. 12, 1990 [IT] Italy ............................. 20629 A/90

[51] Int. Cl.$^5$ .................... C08K 5/357; C08K 5/3492; C08K 5/3472; C07D 231/08; C07D 243/00

[52] U.S. Cl. ........................... 524/96; 524/98; 524/100; 524/106; 540/553; 549/59; 544/115; 544/194; 544/207; 544/219; 544/371; 548/365.1; 548/370.1; 548/370.4; 548/365.7; 548/364.1

[58] Field of Search ............ 524/100, 106, 96, 98; 548/365, 363, 364, 367; 544/371, 115, 207, 219, 194; 549/59; 430/483; 540/553

[56] References Cited

U.S. PATENT DOCUMENTS

| | | | |
|---|---|---|---|
| 3,531,423 | 9/1970 | Stokes et al. | 260/18 |
| 4,491,630 | 1/1985 | Ishikawa et al. | 430/372 |
| 4,845,016 | 7/1989 | Ishikawa et al. | 430/372 |
| 5,079,285 | 1/1992 | Kluttz | 524/106 |

FOREIGN PATENT DOCUMENTS

| | | |
|---|---|---|
| 0014921 | 9/1980 | European Pat. Off. |
| 1912796 | 10/1969 | Fed. Rep. of Germany |
| 53-36539 | 4/1978 | Japan |
| 56-86165 | 7/1981 | Japan |
| 58-139136 | 8/1983 | Japan |
| 59-104641 | 6/1984 | Japan |
| 60-26339 | 2/1985 | Japan |
| 60-46549 | 3/1985 | Japan |
| 62-177555 | 8/1987 | Japan |
| 62-180363 | 8/1987 | Japan |
| 62-234158 | 10/1987 | Japan |
| 62-237450 | 10/1987 | Japan |
| 62-265648 | 11/1987 | Japan |
| 2-016538 | 1/1990 | Japan |
| 2-262649 | 10/1990 | Japan |
| 2073734 | 10/1981 | United Kingdom |

OTHER PUBLICATIONS

CA: 103:45739j (1985).
CA 113:106495g (1990).
CA 102:70094g (1985).
CA 103:79402j (1985).
CA 101:161,153w (1984).
CA 108:177005e (1988).
CA 108:213839r (1988).
CA 109:14586b (1988).
CA 108:104015y (1988).
CA 110:163473k (1989).

*Primary Examiner*—Veronica P. Hoke
*Attorney, Agent, or Firm*—JoAnn Villamizar; William A. Teoli, Jr.

[57] ABSTRACT

The present invention relates to a novel method for stabilizing synthetic thermoplastic materials against thermal degradation, which comprises incorporating in said materials one or more compounds of the formula (I)

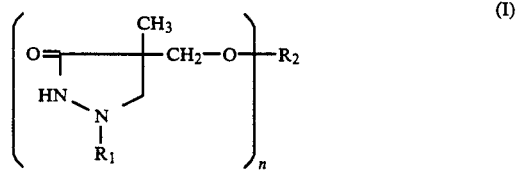

in which $R_1$ is unsubstituted or substituted phenyl, n is e.g. 1, 2 or 3, and, when n is 1, $R_2$ is e.g. —$COR_3$, —$COOR_4$ or —CO-N($R_5$)$R_6$ in which $R_3$ is e.g. $C_4$-$C_{17}$alkyl, $R_4$ is e.g. $C_4$-$C_{18}$alkyl, cyclohexyl or t-butylcyclohexyl, $R_5$ and $R_6$ which can be identical or different are e.g. $C_2$-$C_8$alkyl or cyclohexyl, and, when n is 2, $R_2$ is e.g. —CO—$R_{10}$—OC, —COO-$R_{11}$—OOC— or —CONH—$R_{12}$—NHCO- in which $R_{10}$ is e.g. $C_2$-$C_8$alkylene, $R_{11}$ is e.g. $C_4$-$C_6$alkylene and $R_{12}$ is e.g. $C_4$-$C_6$alkylene, and, when n is 3, $R_2$ is e.g. benzenetricarbonyl.

Several compounds of the formula (I) are new.

10 Claims, No Drawings

METHOD FOR STABILIZING SYNTHETIC THERMOPLASTIC MATERIALS AGAINST THERMAL DEGRADATION

The present invention relates to a novel method for stabilizing synthetic thermoplastic materials against thermal degradation by means of using derivatives of 3-pyrazolidinone as well as to several novel derivatives of 3-pyrazolidinone.

In Japanese Laid Open Print Sho 56-86,165 and in British Laid Open Print 2,073,734, the preparation and the use in the photographic field of some derivatives of 4-hydroxymethyl-4-methyl-1-phenyl-3-pyrazolidinone of the formula $$R-\overset{O}{\underset{\|}{C}}-OCH_2-\overset{CH_3}{\underset{\underset{C_6H_5}{\overset{|}{N}}}{\overset{|}{\underset{NH}{\diagup}}}}=O$$

in which R has various definitions, are described.

In the cited Japanese laid open print, the possibility of using these compounds as antioxidants for plastic materials is also indicated, but no application example or any information on the usefulness of these compounds in practice is reported.

It has now been found that some derivatives of 4-hydroxymethyl-4-methyl-1-phenyl-3-pyrazolidinone, while having a very low long-term antioxidant activity, are surprisingly highly effective as stabilizers against thermal degradation for synthetic thermoplastic materials, especially polyolefins. In particular, the present invention relates to a novel method for stabilizing synthetic thermoplastic materials against thermal degradation, which comprises incorporating in said materials one or more compounds of the formula (I)

$$\left( O=\underset{\underset{R_1}{\overset{|}{N}}}{\underset{HN\diagdown N}{\overset{CH_3}{\overset{|}{\diagup}}}}-CH_2-O-R_2 \right)_n \quad (I)$$

in which $R_1$ is phenyl unsubstituted or substituted by 1, 2 or 3 radicals selected from the group consisting of $C_1-C_4$alkyl, $C_1-C_4$alkoxy and OH; n is 1, 2, 3 or 4 and, when n is 1, $R_2$ is one of the groups of the formulae (IIa)–(IId)

$$-COR_3, \quad (IIa)$$

$$-COOR_4, \quad (IIb)$$

$$-CO-\underset{R_5}{\overset{|}{N}}-R_6, \quad (IIc)$$

$$\underset{X}{\overset{N}{\underset{N}{\overset{\diagup}{\bigcirc}}\diagdown}}Y \quad (IId)$$

in which $R_3$ is hydrogen, $C_1-C_{18}$alkyl, $C_5-C_{12}$cycloalkyl unsubstituted or mono-, di- or tri-substituted by $C_1-C_4$alkyl; $C_2-C_{18}$alkenyl, $C_7-C_9$phenylalkyl unsubstituted or substituted on the phenyl by 1, 2 or 3 radicals selected from the group consisting of $C_1-C_4$alkyl and OH; phenyl unsubstituted or substituted by 1, 2 or 3 radicals selected from the group consisting of $C_1-C_4$alkyl, $C_1-C_4$alkoxy and OH; or a 5-membered to 6-membered heterocyclic group, $R_4$ is $C_1-C_{18}$alkyl, $C_5-C_{12}$cycloalkyl unsubstituted or mono-, di- or tri-substituted by $C_1-C_4$alkyl; $C_3-C_{18}$alkenyl or $C_7-C_9$phenylalkyl unsubstituted or substituted on the phenyl by 1, 2 or 3 radicals selected from the group consisting of $C_1-C_4$alkyl and OH; $R_5$ and $R_6$ which can be identical or different are hydrogen, $C_1-C_{18}$alkyl, $C_5-C_{12}$cycloalkyl unsubstituted or mono-, di- or tri-substituted by $C_1-C_4$alkyl; $C_3-C_{18}$alkenyl, $C_7-C_9$phenylalkyl unsubstituted or substituted on the phenyl by 1, 2 or 3 radicals selected from the group consisting of $C_1-C_4$alkyl and OH; or phenyl unsubstituted or substituted by 1, 2 or 3 radicals selected from the group consisting of $C_1-C_4$alkyl, $C_1-C_4$alkoxy and OH; or $$-\underset{R_5}{\overset{|}{N}}-R_6$$

is a 5-membered to 7-membered heterocyclic group and X and Y which can be identical or different are a group $-OR_7$, $-SR_7$ or $$-\underset{R_8}{\overset{|}{N}}-R_9$$

where $R_7$, $R_8$ and $R_9$ which can be identical or different are hydrogen, $C_1-C_{18}$alkyl, $C_5-C_{12}$cycloalkyl unsubstituted or mono-, di- or tri-substituted by $C_1-C_4$alkyl; $C_3-C_{18}$alkenyl, $C_7-C_9$phenylalkyl unsubstituted or substituted on the phenyl by 1, 2 or 3 radicals selected from the group consisting of $C_1-C_4$alkyl and OH; phenyl unsubstituted or substituted by 1, 2 or 3 radicals selected from the group consisting of $C_1-C_4$alkyl, $C_1-C_4$alkoxy and OH; tetrahydrofurfuryl or $C_2-C_4$alkyl substituted in the 2-, 3- or 4-position by $C_1-C_8$alkoxy or by di-($C_1-C_4$alkyl)amino; or $$-\underset{R_8}{\overset{|}{N}}-R_9$$

is a 5-membered to 7-membered heterocyclic group, and, when n is 2, $R_2$ is carbonyl or one of the groups of the formulae (IIIa)–(IIId)

$$-CO-R_{10}-C-, \quad (IIIa)$$

$$-COO-R_{11}-OOC-, \quad (IIIb)$$

$$-CONH-R_{12}-NHCO-, \quad (IIIc)$$

(IIId)

in which $R_{10}$ is a direct bond, $C_1-C_{12}$alkylene, $C_2-C_{12}$alkylene interrupted by 1, 2 or 3 oxygen atoms or by 1 or 2 >N—$R_{13}$ groups with $R_{13}$ being as defined above for $R_5$ and $R_6$; $C_2-C_{20}$alkylidene, phenyl-($C_1-C_{14}$alkylidene), cyclohexylene, methylcyclohexylene, cyclohexenylene, phenylene, $C_2-C_{18}$alkenylene or a 5-membered to 6-membered heterocyclic group, $R_{11}$ is $C_2-C_{12}$alkylene, $C_4-C_{12}$alkylene interrupted by 1, 2 or 3 oxygen atoms, cyclohexylene, cyclohexylenedimethylene, methylenedicyclohexylene, isopropylidenedicyclohexylene, phenylene, isopropylidenediphenylene or xylylene, $R_{12}$ is as defined above for $R_{11}$ or is tolylene, methylenediphenylene or a group

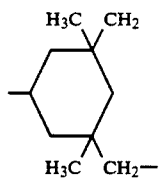

and Z is as defined above for X and Y, and, when n is 3, $R_2$ is aliphatic $C_4-C_{18}$triacyl, aliphatic $C_6-C_{18}$triacyl containing a trisubstituted nitrogen atom; aromatic $C_9-C_{18}$triacyl, heterocyclic triacyl containing up to 18 carbon atoms or 1,3,5-triazine-2,4,6-triyl, and, when n is 4, $R_2$ is aliphatic $C_6-C_{18}$tetraacyl, aliphatic $C_{10}-C_{18}$tetraacyl containing 2 trisubstituted nitrogen atoms; aromatic $C_{10}-C_{18}$tetraacyl or cycloaliphatic $C_{10}-C_{22}$tetraacyl.

In the compounds of the formula (I) n is preferably 1.

Examples of $C_1-C_{18}$alkyl are methyl, ethyl, propyl, isopropyl, butyl, sec-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, pentadecyl, hexadecyl, heptadecyl and octadecyl.

Examples of $C_2-C_4$alkyl substituted by $C_1-C_8$alkoxy, preferably $C_1-C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2-C_4$alkyl substituted by di-($C_1-C_4$alkyl)-amino, preferably dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Representative examples of the various $C_5-C_{12}$cycloalkyl groups which are unsubstituted or mono-, di- or tri-substituted by $C_1-C_4$alkyl; are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl; unsubstituted or $C_1-C_4$alkyl-substituted cyclohexyl is preferred.

Examples of alkenyl having up to 18 carbon atoms are vinyl, allyl, 1-propenyl, 2-methylallyl, butenyl, hexenyl, decenyl, undecenyl, heptadecenyl and octadecenyl.

The various $C_7-C_9$phenylalkyl groups are unsubstituted or e.g. mono-, di- or tri-substituted on the phenyl by $C_1-C_4$alkyl and/or substituted by an OH group; representative examples are benzyl, methylbenzyl, dimethylbenzyl, trimethylbenzyl, t-butylbenzyl, 2-phenylethyl and 2-(3,5-di-t-butyl-4-hydroxyphenyl)-ethyl.

In the various substituted phenyl groups, the substituents on the phenyl can be e.g. 1,2 or 3 $C_1-C_4$alkyl or $C_1-C_4$alkoxy groups and/or an OH group; representative examples are methylphenyl, dimethylphenyl, trimethylphenyl, 3,5-di-t-butyl-4-methylphenyl, methoxyphenyl, ethoxyphenyl, hydroxyphenyl and 3,5-di-t-butyl-4-hydroxyphenyl.

Representative examples of a 5-membered to 6-membered heterocyclic group $R_3$ are furyl, tetrahydrofuryl, thienyl and pyridyl.

Representative examples of 5-membered to 7-membered heterocyclic groups

and

are 1-pyrrolidyl, 1-piperidyl, 4-morpholinyl, 4-methyl-1-piperazinyl and 1-hexahydroazepinyl. 4-Morpholinyl is preferred.

Examples of alkylene having up to 12 carbon atoms are methylene, ethylene, propylene, trimethylene, tetramethylene, pentamethylene, 2,2-dimethyltrimethylene, hexamethylene, heptamethylene, octamethylene, trimethylhexamethylene, decamethylene and dodecamethylene.

Examples of alkylene having up to 12 carbon atoms, interrupted by 1,2 or 3 oxygen atoms, are 2-oxapropane-1,3-diyl, 3-oxapentane-1,5-diyl, 2,5-dioxahexane-1,6-diyl, 3,6-dioxaoctane-1,8-diyl, 2,5,8-trioxanonane-1,9-diyl and 3,6,9-trioxaundecane-1,11-diyl.

Representative examples of $C_2-C_{12}$alkylene $R_{10}$ interrupted by 1 or 2 >$NR_{13}$ groups are the groups

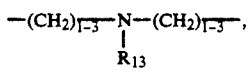

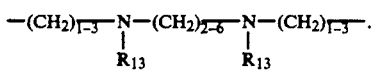

Examples of $C_2-C_{20}$alkylidene are ethylidene, propylidene, butylidene, pentylidene, heptylidene, nonylidene, tridecylidene, pentadecylidene, heptadecylidene, nonadecylidene, 1-methylethylidene, 1-ethylpropylidene or 1-ethylpentylidene.

Examples of phenyl-($C_1-C_{14}$alkylidene) are benzylidene, 2-phenylethylidene, 1-phenyl-2-hexylidene, 1-phenyl-2-decylidene or 1-phenyl-2-tetradecylidene.

Examples of $C_2-C_{18}$alkenylene are vinylene, methylvinylene, octenylethylene or dodecenylethylene.

Representative examples of a 5-membered to 6-membered heterocyclic group $R_{10}$ are furandiyl or pyridinediyl.

Examples of $C_4-C_{18}$triacyl are the triacyl derivatives of methanetricarboxylic, 1,1,2-ethanetricarboxylic, 1,2,3-propanetricarboxylic, citric or 1,2,3-butanetricarboxylic acids.

Examples of aliphatic $C_6$-$C_{18}$triacyl containing a trisubstituted nitrogen atom are the groups N—[—(CH$_2$)$_{1-5}$—CO—]$_3$. The group N—(CH$_2$—CO—)$_3$ is particularly preferred.

Examples of $C_9$-$C_{18}$aromatic triacyl are the triacyl derivatives of 1,2,4-benzenetricarboxylic or 1,3,5-benzenetricarboxylic acids.

Examples of heterocyclic triacyl having up to 18 carbon atoms are

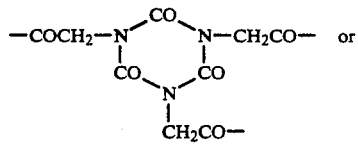

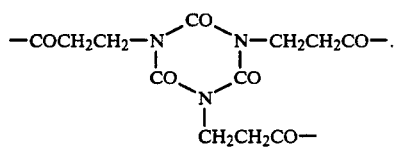

Aliphatic $C_6$-$C_{18}$tetraacyl $R_2$ is, for example, a tetraacyl derivative of 1,1,3,3-propanetetracarboxylic or 1,2,3,4-butanetetracarboxylic acids. Aliphatic $C_{10}$-$C_{18}$tetraacyl $R_2$ containing 2 trisubstituted nitrogen atom is, for example, a group of the formula

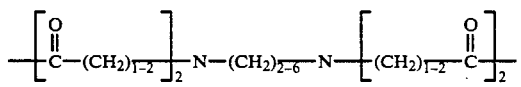

Aromatic $C_{10}$-$C_{18}$tetraacyl $R_2$ is, for example, the tetraacyl derivative of 1,2,4,5-benzenetetracarboxylic acid.

Cycloaliphatic $C_{10}$-$C_{22}$tetraacyl $R_2$ is, for example, one of the groups

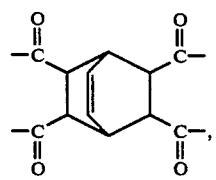

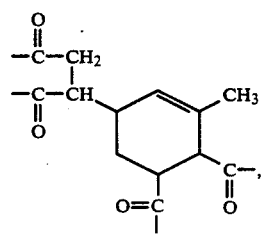

-continued

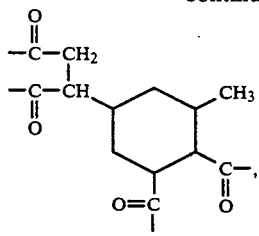

Those compounds of the formula (I) are preferred, in which $R_1$ is phenyl which is unsubstituted or substituted by 1,2 or 3 $C_1$-$C_4$alkyl or $C_1$-$C_4$alkoxy groups; n is 1, 2, 3 or 4 and, when n is 1, $R_2$ is one of the groups of the formulae (IIa)-(IId) in which $R_3$ is hydrogen, $C_1$-$C_{17}$alkyl, $C_5$-$C_8$cycloalkyl unsubstituted or mono-, di- or tri-substituted by $C_1$-$C_4$alkyl; $C_2$-$C_{17}$alkenyl, benzyl or phenylethyl which is unsubstituted or substituted on the phenyl by 1,2 or 3 radicals selected from the group consisting of $C_1$-$C_4$alkyl and OH; or phenyl which is unsubstituted or substituted by 1,2 or 3 radicals selected from the group consisting of $C_1$-$C_4$alkyl and OH; furyl, thienyl or pyridyl, $R_4$ is $C_1$-$C_{18}$alkyl, $C_5$-$C_8$cycloalkyl unsubstituted or mono-, di- or tri-substituted by $C_1$-$C_4$alkyl; $C_3$-$C_{18}$alkenyl or benzyl, $R_5$ and $R_6$ which can be identical or different are hydrogen, $C_1$-$C_{18}$alkyl, $C_5$-$C_8$cycloalkyl unsubstituted or mono-, di- or tri-substituted by $C_1$-$C_4$alkyl; $C_3$-$C_{18}$alkenyl, benzyl or phenyl, or

is 1-pyrrolidyl, 1-piperidyl, 4-morpholinyl or 1-hexahydroazepinyl, X and Y which can be identical or different are a group —OR$_7$, —SR$_7$ or

where $R_7$, $R_8$ and $R_9$ which can be identical or different are hydrogen, $C_1$-$C_{12}$alkyl, $C_5$-$C_8$cycloalkyl unsubstituted or mono-, di- or tri-substituted by $C_1$-$C_4$alkyl; $C_3$-$C_{12}$alkenyl, benzyl, phenyl, tetrahydrofurfuryl, $C_2$-$C_3$alkyl substituted in the 2- or 3-position by $C_1$-$C_4$alkoxy or by di-($C_1$-$C_4$alkyl)-amino; or

is 1-pyrrolidyl, 1-piperidyl, 4-morpholinyl or 1-hexahydroazepinyl, and, when n is 2, $R_2$ is one of the groups of the formulae (IIIa)-(IIId) in which $R_{10}$ is a direct bond, $C_1$-$C_{12}$alkylene, $C_2$-$C_{10}$alkylene interrupted by 1,2 or 3 oxygen atoms or by 1 or 2 >N—$R_{13}$ groups with $R_{13}$ being as defined above for $R_5$ and $R_6$; $C_2$-$C_{19}$alkylidene, phenyl-($C_1$-$C_{14}$alkylidene), cyclohexylene, methylcyclohexylene, cyclohexenylene, phenylene, $C_2$-$C_{16}$alkenylene, furandiyl or pyridinediyl, $R_{11}$ is $C_2$-$C_{12}$alkylene, $C_4$-$C_{10}$alkylene interrupted by 1, 2 or 3 oxygen atoms, cyclohexylene, cyclohexylenedimethylene, methylenedicyclohexylene, isopropylidenedicyclohexylene, phenylene, isopropylidenediphenylene or xylylene, $R_{12}$ is as defined above for $R_{11}$ or is tolylene, methylenediphenylene or a group

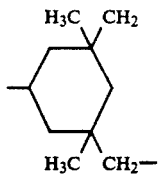

and Z is as defined above for X and Y, and, when n is 3, $R_2$ is aliphatic $C_4$-$C_{12}$triacyl, a group $N(CH_2CO—)_3$, aromatic $C_9$-$C_{12}$triacyl, heterocyclic triacyl having up to 12 carbon atoms or a 1,3,5-triazine-2,4,6-triyl group and, when n is 4, $R_2$ is aliphatic $C_6$-$C_{12}$tetraacyl or aromatic $C_{10}$-$C_{12}$tetraacyl.

Those compounds of the formula (I) are particularly preferred, in which $R_1$ is phenyl, n is 1, 2 or 3 and, when n is 1, $R_2$ is one of the groups of the formulae (IIa)–(IId) in which $R_3$ is $C_1$-$C_{17}$alkyl, cyclohexyl which is unsubstituted or mono-, di- or tri-substituted by $C_1$-$C_4$alkyl; $C_2$-$C_{10}$alkenyl, benzyl, 2-(3,5-di-t-butyl-4-hydroxyphenyl)-ethyl, phenyl, t-butylphenyl, 3,5-di-t-butyl-4-hydroxyphenyl, furyl or pyridyl, $R_4$ is $C_1$-$C_{18}$alkyl, cyclohexyl which is unsubstituted or mono-, di- or tri-substituted by $C_1$-$C_4$alkyl; allyl, oleyl or benzyl, $R_5$ and $R_6$ which can be identical or different are hydrogen, $C_1$-$C_{12}$alkyl, cyclohexyl which is unsubstituted or mono-, di- or tri-substituted by $C_1$-$C_4$alkyl; allyl, benzyl or

is 4-morpholinyl, X and Y which can be identical or different are a group $—OR_7$, $—SR_7$ or $$—\underset{R_8}{\underset{|}{N}}—R_9$$

where $R_7$, $R_8$ and $R_9$ which can be identical or different are $C_1$-$C_{12}$alkyl, cyclohexyl which is unsubstituted or mono-, di- or tri-substituted by $C_1$-$C_4$alkyl; allyl, undecenyl, benzyl, phenyl, tetrahydrofurfuryl, $C_2$-$C_3$alkyl substituted in the 2- or 3-position by $C_1$-$C_4$alkoxy, by dimethylamino or by diethylamino; or $R_8$ can also be hydrogen, or

is 4-morpholinyl, and, when n is 2, $R_2$ is one of the groups of the formulae (IIIa)–(IIId) in which $R_{10}$ is a direct bond, $C_1$-$C_{10}$alkylene, $C_2$-$C_8$alkylene interrupted by 1, 2 or 3 oxygen atoms or by 1 or 2 $>N—R_{13}$ groups with $R_{13}$ being as defined above for $R_5$ and $R_6$; $C_2$-$C_{15}$alkylidene, phenyl-($C_1$-$C_{10}$alkylidene), cyclohexylene, cyclohexenylene, phenylene or $C_2$-$C_{14}$alkenylene, $R_{11}$ is $C_2$-$C_{10}$alkylene, $C_4$-$C_8$alkylene interrupted by 1 or 2 oxygen atoms; cyclohexylenedimethylene, methylenedicyclohexylene, isopropylidenedicyclohexylene or isopropylidenediphenylene, $R_{12}$ is as defined above for $R_{11}$ or tolylene, methylenediphenylene or a group

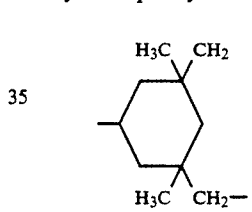

and Z is as defined above for X and Y, and, when n is 3, $R_2$ is aliphatic $C_4$-$C_7$triacyl, a group $N(CH_2—CO—)_3$, aromatic $C_9$-$C_{10}$triacyl, or a 1,3,5-triazine-2,4,6-triyl group.

Compounds of the formula (I) which are of special interest are those in which $R_1$ is phenyl, n is 1, 2 or 3 and, when n is 1, $R_2$ is one of the groups of the formulae (IIa)–(IIc) in which $R_3$ is $C_3$-$C_{17}$alkyl, cyclohexyl, $C_2$-$C_{10}$alkenyl, 2-(3,5-di-t-butyl-4-hydroxyphenyl)ethyl, phenyl or 3,5-di-t-butyl-4-hydroxyphenyl, $R_4$ is $C_2$-$C_{18}$alkyl, cyclohexyl, trimethylcyclohexyl, t-butylcyclohexyl or allyl, $R_5$ and $R_6$ which can be identical or different are hydrogen, $C_1$-$C_{12}$alkyl, cyclohexyl or benzyl, and, when n is 2, $R_2$ is one of the groups of the formulae (IIIa)–(IIIc) in which $R_{10}$ is a direct bond, $C_1$-$C_8$alkylene, $C_4$-$C_{13}$alkylidene, phenyl-($C_1$-$C_8$alkylidene), cyclohexylene, cyclohexenylene, phenylene or vinylene, $R_{11}$ is $C_4$-$C_8$alkylene, cyclohexylenedimethylene, isopropylidenedicyclohexylene or isopropylidenediphenylene, $R_{12}$ is as defined above for $R_{11}$ or is methylenedicyclohexylene, tolylene, methylenediphenylene or a group and, when n is 3, $R_2$ is aliphatic $C_5$-$C_7$triacyl, a group $N(CH_2CO—)_3$ or benzenetricarbonyl.

Those compounds of the formula (I) are of particular interest, in which $R_1$ is phenyl, n is 1, 2 or 3 and, when n is 1, $R_2$ is one of the groups of the formulae (IIa)–(IIc) in which $R_3$ is $C_4$-$C_{17}$alkyl, $R_4$ is $C_4$-$C_{18}$alkyl, cyclohexyl or t-butylcyclohexyl, $R_5$ and $R_6$ which can be identical or different are $C_2$-$C_8$alkyl or cyclohexyl and $R_5$ can also be hydrogen, and, when n is 2, $R_2$ is one of the groups of the formulae (IIIa)–(IIIc) in which $R_{10}$ is $C_2$-$C_8$alkylene, $R_{11}$ is $C_4$-$C_6$alkylene and $R_{12}$ is $C_4$-$C_6$alkylene, and, when n is 3, $R_2$ is benzenetricarbonyl.

The compounds of the formula (I) can be prepared by known processes, for example as reported in Japanese Laid Open Print Sho 56-86,165 and in British Laid Open Print 2,073,734, by reacting, in the appropriate molar ratios, a compound of the formula (IV)

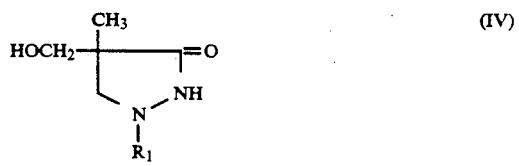

with a compound of the formula (V)

where $R_2$ is as defined above and A is e.g. Cl, Br or I, or $R_2(A)_n$ is a mono- or di-isocyanate. The reactions are conveniently carried out in an organic solvent, for example tetrahydrofuran, dioxane, dibutyl ether, benzene, toluene, xylene, dichloromethane or acetonitrile, operating at a temperature between e.g. 0° and 200° C., preferably between 5° and 100° C.

The compounds of the formula (IV) and those of the formula (V) are commercial products or can easily be prepared by known processes.

A further embodiment of the instant invention are the novel compounds of the formula (Ia)

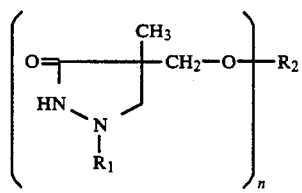
(Ia)

in which $R_1$ is phenyl unsubstituted or substituted by 1, 2 or 3 radicals selected from the group consisting of $C_1$–$C_4$alkyl, $C_1$–$C_4$alkoxy and OH; n is 1, 2, 3 or 4 and, when n is 1, $R_2$ is a group of the formula (IId)

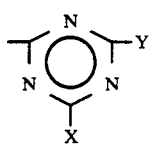
(IId)

in which X and Y which can be identical or different are a group —$OR_7$, —$SR_7$ or

where $R_7$, $R_8$ and $R_9$ which can be identical or different are hydrogen, $C_1$–$C_{18}$alkyl, $C_5$–$C_{12}$cycloalkyl unsubstituted or mono-, di- or tri-substituted by $C_1$–$C_4$alkyl; $C_3$–$C_{18}$alkenyl, $C_7$–$C_9$phenylalkyl unsubstituted or substituted on the phenyl by 1, 2 or 3 radicals selected from the group consisting of $C_1$–$C_4$alkyl and OH; phenyl unsubstituted or substituted by 1, 2 or 3 radicals selected from the group consisting of $C_1$–$C_4$alkyl, $C_1$–$C_4$alkoxy and OH; tetrahydrofurfuryl, $C_2$–$C_4$alkyl substituted in the 2-, 3- or 4-position by $C_1$–$C_8$alkoxy or by di-($C_1$–$C_4$alkyl)-amino; or

is a 5-membered to 7-membered heterocyclic group, and, when n is 2, $R_2$ is carbonyl or one of the groups of the formulae (IIIa)–(IIId)

—CO—$R_{10}$—CO—,  —COO$R_{11}$—OOC—,
(IIIa)           (IIIb)

—CONH—$R_{12}$—NHCO—,
(IIIc)

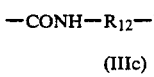
(IIId)

in which $R_{10}$ is a direct bond, $C_1$–$C_{12}$alkylene, $C_2$–$C_{12}$alkylene interrupted by 1, 2 or 3 oxygen atoms or by 1 or 2 >N—$R_{13}$ groups; $C_2$–$C_{20}$alkylidene, phenyl-($C_1$–$C_{14}$alkylidene), cyclohexylene, methylcyclohexylene, cyclohexenylene, phenylene, $C_2$–$C_{18}$alkenylene or a 5-membered to 6-membered heterocyclic group, $R_{13}$ is hydrogen, $C_1$–$C_{18}$alkyl, $C_5$–$C_{12}$cycloalkyl unsubstituted or mono-, di- or tri-substituted by $C_1$–$C_4$alkyl; $C_3$–$C_{18}$alkenyl, $C_7$–$C_9$phenylalkyl unsubstituted or substituted on the phenyl by 1, 2 or 3 radicals selected from the group consisting of $C_1$–$C_4$alkyl and OH; or phenyl unsubstituted or substituted by 1, 2 or 3 radicals selected from the group consisting of $C_1$–$C_4$alkyl, $C_1$–$C_4$alkoxy and OH; $R_{11}$ is $C_2$–$C_{12}$alkylene, $C_4$–$C_{12}$alkylene interrupted by 1, 2 or 3 oxygen atoms; cyclohexylene, cyclohexylenedimethylene, methylenedicyclohexylene, isopropylidenedicyclohexylene, phenylene, isopropylidenediphenylene or xylylene, $R_{12}$ is as defined above for $R_{11}$ or is tolylene, methylenediphenylene or a group

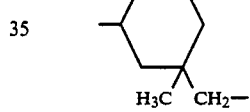

and Z is as defined above for X and Y, and, when n is 3, $R_2$ is aliphatic $C_4$–$C_{18}$triacyl, aliphatic $C_6$–$C_{18}$triacyl containing a trisubstituted nitrogen atom; aromatic $C_9$–$C_{18}$triacyl, heterocyclic triacyl having up to 18 carbon atoms or 1,3,5-triazine-2,4,6-triyl, and, when n is 4, $R_2$ is aliphatic $C_6$–$C_{18}$tetraacyl, aliphatic $C_{10}$–$C_{18}$tetraacyl containing 2 trisubstituted nitrogen atoms; aromatic $C_{10}$–$C_{18}$tetraacyl or cycloaliphatic $C_{10}$–$C_{22}$tetraacyl.

As mentioned at the outset, the compounds of the formula (I) are highly effective in stabilizing synthetic thermoplastic materials against thermal degradation.

Examples of polymeric materials which can be stabilized are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers mentioned in 1) above, for example polypropylene/ethylene-propylene copolymers, LDPE/EVA, LDPE/EAA, LLDPE/EVA and LLDPE/EAA.

3a. Copolymers of α-olefins with carbon monoxide, with regular or random alternation.

3b. Hydrocarbon resins (for example $C_5$–$C_9$) and hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from copolymers of styrene and other polymers, such as, for example, from a polyacrylate, a diene polymer or an ethylene/propylene/diene terpolymer and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene; styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene; styrene and alkyl acrylates or methacrylates on polybutadiene; styrene and acrylonitrile on ethylene/propylene/diene terpolymers; styrene and acrylonitrile on polyacrylates or polymethacrylates; styrene and acrylonitrile on acrylate/butadiene copolymers, as well as mixtures thereof with the copolymers listed under 5), for instance the mixtures known as ABS, MBS, ASA and AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, such as for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene and polyamides.

14. Polyurethanes which are derived from polyethers, polyesters or polybutadiene with terminal hydroxyl groups on the one hand and aliphatic or aromatic polyisocyanates on the other hand, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6/6, polyamide 6/10, 6/9, 6/12 and 4/6, polyamide 11, polyamide 12, aromatic polyamides obtained by condensation of m-xylenediamine and adipic acid; polyamides prepared from hexamethylenediamine and isophthalic and/or terephthalic acid and optionally an elastomer as modifier, for example poly-2,4,4-trimethyl-hexamethyleneterephthalamide or poly-m-phenylene-isophthalamide. Further, copolymers of the aforementioned polyamides with polyolefins, olefin copolymers, ionomers or chemically bonded or grafted elastomers; or with polyethers, as, for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-(4-hydroxyphenyl)-propane]terephthalate and polyhydroxybenzoate as well as block copolyether-esters derived from polyethers having hydroxyl end groups.

18. Polycarbonates and polyester-carbonates.

19. Polysulfones, polyether-sulfones and polyether-ketones.

20. Natural polymers, such as cellulose, rubber, and derivatives thereof which are chemically modified in a polymer-homologous manner, such as cellulose acetates, cellulose propionates and cellulose butyrates, or cellulose ethers, such as methylcellulose.

21. Mixtures of the polymers mentioned above, for example PP/EPDM, polyamide 6/EPDM or ABS, PVC/EVA, PVC/ABS, PVC/MBS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6/6 and copolymers, PA/HDPE, PA/PP, PA/PPE.

The compounds of the formula (I) are particularly suitable for improving the resistance to thermal degradation of polyolefins, in particular polyethylene and polypropylene.

The compounds of the formula (I) can be used in mixtures with synthetic thermoplastic mateials in various proportions depending on the nature of the material to be stabilized, on the end use and on the presence of other additives.

In general, it is appropriate to use, for example, 0.001 to 1% by weight of the compounds of the formula (I), relative to the weight of the material to be stabilized, preferably between 0.01 and 0.5%.

The compounds of the formula (I) can be incorporated in the synthetic thermoplastic materials before, during or after the polymerization or crosslinking of the said materials.

The compounds of the formula (I) can be incorporated in the synthetic thermoplastic materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilized with the products of the formula (I) can be used for the production of mouldings, films, tapes, monofilaments, fibres and the like.

If desired, other conventional additives for synthetic thermoplastic materials, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the synthetic thermoplastic materials.

Particular examples of additives which can be used in admixture with the compounds of the formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha$,$\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)-dicyclopentadiene, bis[2-(3'-tert-butyl-2'-hydroxy-5'-methylbenzyl)-6-tert-butyl-4-methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example lauric acid 4-hydroxyanilide, stearic acid 4-hydroxyanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

1.7. Esters of $\beta$-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxamide.

1.8. Esters of $\beta$-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'bis(hydroxyethyl)oxamide.

1.9. Esters of $\beta$-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxamide.

1.10. Amides of $\beta$-(3,5-di-tert-butyl-4-hydroxyphenyl)propionic acid e.g.
   N,N'-bis(3,5-di-tert-butyl-4-hydroxyphenylpropionyl)-hexamethylenediamine,
   N,N'-bis(3,5-di-tert-butyl-4-hydroxyphenylpropionyl)-trimethylenediamine,
   N,N'-bis(3,5-di-tert-butyl-4-hydroxyphenylpropionyl)-hydrazine.

2. UV absorbers and light stabilizers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis($\alpha$,$\alpha$-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of variously substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tertbutylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2′thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Oxalic acid diamides, for example, 4,4′-dioctyloxyoxanilide, 2,2′-dioctyloxy-5,5′-di-tert-butyloxanilide, 2,2′-didodecyloxy-5,5′-di-tert-butyloxanilide, 2-ethoxy-2′-ethyloxanilide, N,N′-bis(3-dimethylaminopropyl)oxamide, 2-ethoxy-5-tert-butyl-2′-ethyloxanilide and its mixtures with 2-ethoxy-2′-ethyl-5,4′-di-tert-butyloxanilide and mixtures of ortho- and para-methoxy-disubstituted oxanilides and mixtures of o- and p-ethoxy-disubstituted oxanilides.

2.7 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N′-diphenyloxamide, N-salicylal-N′-salicyloylhydrazne, N,N′-bis(-salicyloyl)hydrazine, N,N′-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4′-biphenylenediphosphonite, 3,9-bis(2,4-di-tert-butylphenoxy)-2,4,8,10-tetraoxa-3,9-diphosphaspiro[5.5]undecane.

4a. Hydroxylamines, for example dibenzylhydroxylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate or bis-(1-hydroxy-2,2,6,6-tetramethyl-4-piperidyl) sebacate.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticizers, lubricants, emulsifiers, pigments, optical brighteners, flame-proofing agents, antistatic agents and blowing agents.

Several examples of the preparation and use of the compounds of the formula (I) as stabilizers are reported for more detailed illustration of the present invention; these examples are given solely for illustrative purposes and do not imply any restriction.

Especially preferred compounds of the formula (I) are those described in Examples 4 and 5.

EXAMPLE 1

Preparation of

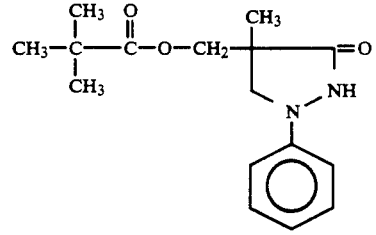

16.48 g (0.08 mol) of 4-hydroxymethyl-4-methyl-1-phenyl-3-pyrazolidinone and 9.64 g (0.08 mol) of pivaloyl chloride in 200 ml of benzene are heated under reflux for 8 hours, with removal of the hydrogen chloride formed.

The reaction mixture is then evaporated under reduced pressure and the residue is recrystallized from ethanol. The product obtained melts at 121°–125° C.

EXAMPLE 2

Preparation of

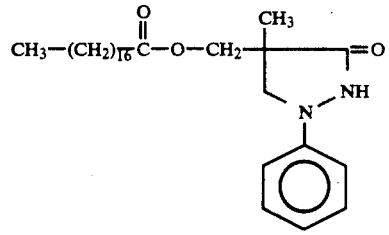

20.6 g (0.1 mol) of 4-hydroxymethyl-4-methyl-1-phenyl-3-pyrazolidinone and 30.29 g (0.1 mol) of stearoyl chloride in 150 ml of toluene are heated for 8 hours at 80° C. in a stream of nitrogen, removing the hydrogen chloride formed. The reaction mixture is then evaporated under reduced pressure and the residue is recrystallized from ethanol.

The product obtained melts at 72°–76° C.

EXAMPLE 3

Preparation of

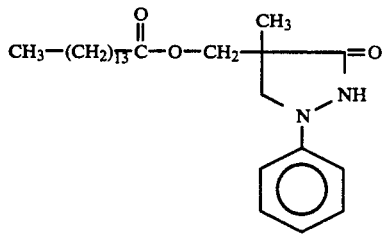

27.60 g (0.1 mol) of tetradecyl chloroformate, dissolved in 50 ml of dichloromethane, are added in the course of 1 hour to a solution, cooled to 5° C., of 20.60 g (0.1 mol) of 4-hydroxymethyl-4-methyl-1-phenyl-3-pyrazolidinone and 11.10 g (0.11 mol) of triethylamine in 150 ml of dichloromethane.

The temperature is allowed to rise to 20° C. and, after standing overnight at this temperature, the mixture is heated for 4 hours at 35°–40° C. After cooling to ambient temperature, the reaction mixture is washed three times with 100 ml of water, dried over $Na_2SO_4$ and then evaporated under reduced pressure.

The residue obtained is recrystallized from hexane.

The product melts at 64°–66° C.

EXAMPLE 4

Preparation of

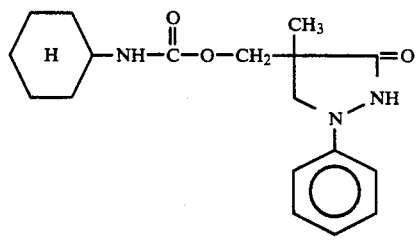

A mixture of 20.60 g (0.1 mol) of 4-hydroxymethyl-4-methyl-1-phenyl-3-pyrazolidinone, 12.50 g (0.1 mol) of cyclohexyl isocyanate and 0.20 g of p-toluenesulfonic acid in 150 ml of toluene and 20 ml of dichloromethane is heated for 6 hours at 60° C. After cooling to ambient temperature, the reaction mixture is washed with water until neutral, dried over $Na_2SO_4$ and evaporated under reduced pressure. The residue obtained is dissolved in dichloromethane and purified by chromatography over silica gel, eluting with acetone. The product melts at 67°–71° C.

EXAMPLE 5

Preparation of

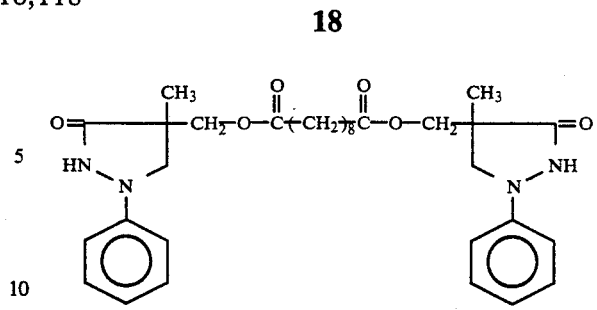

11.95 g (0.05 mol) of sebacoyl chloride dissolved in 100 ml of benzene are added slowly to a mixture of 20.60 g (0.1 mol) of 4-hydroxymethyl-1-phenyl-3-pyrazolidinone and 200 ml of benzene. After the end of the addition, the mixture is heated under reflux for 8 hours in a stream of nitrogen, removing the hydrogen chloride formed.

The reaction mixture is then evaporated under reduced pressure. The residue obtained is purified by chromatography on silica gel, eluting with a 2:1 toluene/acetonitrile mixture.

The product melts at 115°–118° C.

EXAMPLE 6

Process stabilization of polypropylene at 280° C.): 1 g of each of the compounds indicated in Table 1, 0.5 g of pentaerythritol tetrakis-[3-(3,5-di-t-butyl-4-hydroxyphenyl)-propionate] (antioxidant) and 1 g of calcium stearate are mixed in a slow mixer with 1000 g of polypropylene powder of melt flow index=2.10/10 minutes (measured at 230° C./2.16 kg). The mixtures obtained are extruded using an extruder having the following characteristics:

| | |
|---|---|
| internal diameter | 25 mm |
| L/D ratio | 25 |
| rpm | 64 |
| head temperature | 280° C. |

The obtained polymer granules are extruded another 4 times. The melt flow index at 230° C./2.16 kg is measured on the granules obtained after the first, third and fifth extrusion.

The values obtained are reported in Table 1.

TABLE 1

| | Melt flow index after | | |
|---|---|---|---|
| Stabilizer | 1 extrusion | 3 extrusions | 5 extrusions |
| without compounds of the present invention | 4.3 | 12.1 | (a) |
| Compound from Example 1 | 2.1 | 2.7 | 3.9 |
| Compound from Example 2 | 2.1 | 2.9 | 4.2 |
| Compound from Example 3 | 2.1 | 3.0 | 4.0 |
| Compound from Example 4 | 2.1 | 2.7 | 3.8 |
| Compound from Example 5 | 2.1 | 2.6 | 3.4 |

(a)not determinable

A small difference between the melt flow index values after the first and fifth extrusion indicates only a slight degradation of the polymer.

What is claimed is:

1. A method for stabilizing a synthetic thermoplastic material against thermal degradation, which comprises incorporating in said material one or more compounds of the formula (I)

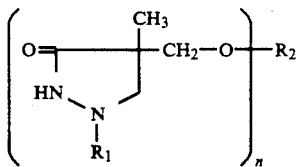

(I)

in which $R_1$ is phenyl unsubstituted or substituted by 1, 2 or 3 radicals selected from the group consisting of $C_1$–$C_4$alkyl, $C_1$–$C_4$alkoxy and OH; n is 1, 2, 3 or 4 and, when n is 1, $R_2$ is one of the groups of the formulae (IIa)–(IId)

—COR$_3$, (IIa)

—COOR$_4$, (IIb)

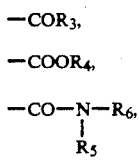 (IIc)

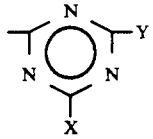 (IId)

in which $R_3$ is hydrogen, $C_1$–$C_{18}$alkyl, $C_5$–$C_{12}$cycloalkyl unsubstituted or mono-, di- or tri-substituted by $C_1$–$C_4$alkyl; $C_2$–$C_{18}$alkenyl, $C_7$–$C_9$phenylalkyl unsubstituted or substituted on the phenyl by 1, 2 or 3 radicals selected from the group consisting of $C_1$–$C_4$alkyl and OH; phenyl unsubstituted or substituted by 1, 2 or 3 radicals selected from the group consisting of $C_1$–$C_4$alkyl, $C_1$–$C_4$alkoxy and OH; or a 5-membered to 6-membered heterocyclic group, $R_4$ is $C_1$–$C_{18}$alkyl, $C_5$–$C_{12}$cycloalkyl unsubstituted or mono-, di- or tri-substituted by $C_1$–$C_4$alkyl; $C_3$–$C_{18}$alkenyl or $C_7$–$C_9$phenylalkyl unsubstituted or substituted on the phenyl by 1, 2 or 3 radicals selected from the group consisting of $C_1$–$C_4$alkyl and OH; $R_5$ and $R_6$ which can be identical or different are hydrogen, $C_1$–$C_{18}$alkyl, $C_5$–$C_{12}$cycloalkyl unsubstituted or mono-, di- or tri-substituted by $C_1$–$C_4$alkyl; $C_3$–$C_{18}$alkenyl, $C_7$–$C_9$phenylalkyl unsubstituted or substituted on the phenyl by 1, 2 or 3 radicals selected from the group consisting of $C_1$–$C_4$alkyl and OH; or phenyl unsubstituted or substituted by 1, 2 or 3 radicals selected from the group consisting of $C_1$–$C_4$alkyl, $C_1$–$C_4$alkoxy and OH; or

is a 5-membered to 7-membered heterocyclic group and X and Y which can be identical or different are a group —OR$_7$, —SR$_7$ or

where $R_7$, $R_8$ and $R_9$ which can be identical or different are hydrogen, $C_1$–$C_{18}$alkyl, $C_5$–$C_{12}$cycloalkyl unsubstituted or mono-, di- or tri-substituted by $C_1$–$C_4$alkyl; $C_3$–$C_{18}$alkenyl, $C_7$–$C_9$phenylalkyl unsubstituted or substituted on the phenyl by 1, 2 or 3 radicals selected from the group consisting of $C_1$–$C_4$alkyl and OH; phenyl unsubstituted or substituted by 1, 2 or 3 radicals selected from the group consisting of $C_1$–$C_4$alkyl, $C_1$–$C_4$alkoxy and OH; tetrahydrofurfuryl or $C_2$–$C_4$alkyl substituted in the 2-, 3- or 4-position by $C_1$–$C_8$alkoxy or by di-($C_1$–$C_4$alkyl)amino; or

is a 5-membered to 7-membered heterocyclic group, and, when n is 2, $R_2$ is carbonyl or one of the groups of the formulae (IIIa)–(IIId)

—CO—R$_{10}$—C—, (IIIa)

—COO—R$_{11}$—OOC—, (IIIb)

—CONH—R$_{12}$—NHCO—, (IIIc)

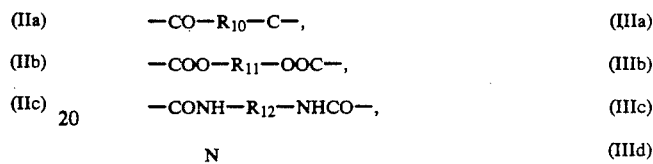 (IIId)

in which $R_{10}$ is a direct bond, $C_1$–$C_{12}$alkylene, $C_2$–$C_{12}$alkylene interrupted by 1, 2 or 3 oxygen atoms or by 1 or 2 >N—$R_{13}$ groups with $R_{13}$ being as defined above for $R_5$ and $R_6$; $C_2$–$C_{20}$alkylidene, phenyl-($C_1$–$C_{14}$alkylidene), cyclohexylene, methylcyclohexylene, cyclohexenylene, phenylene, $C_2$–$C_{18}$alkenylene or a 5-membered to 6-membered heterocyclic group, $R_{11}$ is $C_2$–$C_{12}$alkylene, $C_4$–$C_{12}$alkylene interrupted by 1, 2 or 3 oxygen atoms, cyclohexylene, cyclohexylenedimethylene, methylenedicyclohexylene, isopropylidenedicyclohexylene, phenylene, isopropylidenediphenylene or xylylene, $R_{12}$ is as defined above for $R_{11}$ or is tolylene, methylenediphenylene or a group

and Z is as defined above for X and Y, and, when n is 3, $R_2$ is aliphatic $C_4$–$C_{18}$triacyl, aliphatic $C_6$–$C_{18}$triacyl containing a trisubstituted nitrogen atom; aromatic $C_9$–$C_{18}$triacyl, heterocyclic triacyl containing up to 18 carbon atoms or 1,3,5-triazine-2,4,6-triyl, and, when n is 4, $R_2$ is aliphatic $C_6$–$C_{18}$tetraacyl, aliphatic $C_{10}$–$C_{18}$tetraacyl containing 2 trisubstituted nitrogen atoms; aromatic $C_{10}$–$C_{18}$tetraacyl or cycloaliphatic $C_{10}$–$C_{22}$tetraacyl.

2. A method according to claim 1, in which $R_1$ is phenyl which is unsubstituted or substituted by 1, 2 or 3 $C_1$–$C_4$alkyl or $C_1$–$C_4$alkoxy groups; n is 1, 2, 3 or 4 and, when n is 1, $R_2$ is one of the groups of the formulae (IIa)–(IId) in which $R_3$ is hydrogen, $C_1$–$C_{17}$alkyl, $C_5$–$C_8$cycloalkyl unsubstituted or mono-, di- or tri-substituted by $C_1$–$C_4$alkyl; $C_2$–$C_{17}$alkenyl, benzyl or phenylethyl which is unsubstituted or substituted on the phenyl by 1, 2 or 3 radicals selected from the group consisting of $C_1$–$C_4$alkyl and OH; or phenyl which is unsubstituted or substituted by 1, 2 or 3 radicals selected from the group consisting of $C_1$-$C_4$alkyl and OH; furyl, thienyl or pyridyl, $R_4$ is $C_1$-$C_{18}$alkyl, $C_5$-$C_8$cycloalkyl unsubstituted or mono-, di- or tri-substituted by $C_1$-$C_4$alkyl; $C_3$-$C_{18}$alkenyl or benzyl, $R_5$ and $R_6$ which can be identical or different are hydrogen, $C_1$-$C_{18}$alkyl, $C_5$-$C_8$cycloalkyl unsubstituted or mono-, di- or tri-substituted by $C_1$-$C_4$alkyl; $C_3$-$C_{18}$alkenyl, benzyl or phenyl, or

is 1-pyrrolidyl, 1-piperidyl, 4-morpholinyl or 1-hexahydroazepinyl, X and Y which can be identical or different are a group —OR$_7$, —SR$_7$ or

where $R_7$, $R_8$ and $R_9$ which can be identical or different are hydrogen, $C_1$-$C_{12}$alkyl, $C_5$-$C_8$cycloalkyl unsubstituted or mono-, di- or tri-substituted by $C_1$-$C_4$alkyl; $C_3$-$C_{12}$alkenyl, benzyl, phenyl, tetrahydrofurfuryl, $C_2$-$C_3$alkyl substituted in the 2- or 3-position by $C_1$-$C_4$alkoxy or by di-($C_1$-$C_4$alkyl)-amino; or

is 1-pyrrolidyl, 1-piperidyl, 4-morpholinyl or 1-hexahydroazepinyl, and, when n is 2, $R_2$ is one of the groups of the formulae (IIIa)-(IIId) in which $R_{10}$ is a direct bond, $C_1$-$C_{12}$alkylene, $C_2$-$C_{10}$alkylene interrupted by 1, 2 or 3 oxygen atoms or by 1 or 2>N—$R_{13}$ groups with $R_{13}$ being as defined above for $R_5$ and $R_6$; $C_2$-$C_{19}$alkylidene, phenyl-($C_1$-$C_{14}$alkylidene), cyclohexylene, methylcyclohexylene, cyclohexenylene, phenylene, $C_2$-$C_{16}$alkenylene, furandiyl or pyridinediyl, $R_{11}$ is $C_2$-$C_{12}$alkylene, $C_4$-$C_{10}$alkylene interrupted by 1, 2 or 3 oxygen atoms, cyclohexylene, cyclohexylenedimethylene, methylenedicyclohexylene, isopropylidenedicyclohexylene, phenylene, isopropylidenediphenylene or xylylene, $R_{12}$ is as defined above for $R_{11}$ or is tolylene, methylenediphenylene or a group

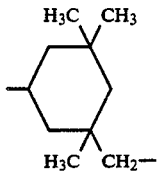

and Z is as defined above for X and Y, and, when n is 3, $R_2$ is aliphatic $C_4$-$C_{12}$triacyl, a group N(CH$_2$CO—)$_3$, aromatic $C_9$-$C_{12}$triacyl, heterocyclic triacyl having up to 12 carbon atoms or a 1,3,5-triazine-2,4,6-triyl group, and when n is 4, $R_2$ is aliphatic $C_6$-$C_{12}$tetraacyl or aromatic $C_{10}$-$C_{12}$tetraacyl.

3. A method according to claim 1, in which $R_1$ is phenyl, n is 1, 2 or 3 and, when n is 1, $R_2$ is one of the groups of the formulae (IIa)-(IId) in which $R_3$ is $C_1$-$C_{17}$ alkyl, cyclohexyl which is unsubstituted or mono-, di- or tri-substituted by $C_1$-$C_4$alkyl; $C_2$-$C_{10}$alkenyl, benzyl, 2-(3,5-di-t-butyl-4-hydroxyphenyl)-ethyl,- phenyl, t-butylphenyl, 3,5-di-t-butyl-4-hydroxyphenyl, furyl or pyridyl, $R_4$ is $C_1$-$C_{18}$alkyl, cyclohexyl which is unsubstituted or mono-, di- or tri-substituted by $C_1$-$C_4$alkyl; allyl, oleyl or benzyl, $R_5$ and $R_6$ which can be identical or different are hydrogen, $C_1$-$C_{12}$alkyl, cyclohexyl which is unsubstituted or mono-, di- or tri-substituted by $C_1$-$C_4$alkyl; allyl, benzyl or

is 4-morpholinyl, X and Y which can be identical or different are a group —OR$_7$, —SR$_7$ or

where $R_7$, $R_8$ and $R_9$ which can be identical or different are $C_1$-$C_{12}$alkyl, cyclohexyl which is unsubstituted or mono-, di- or tri-substituted by $C_1$-$C_4$alkyl; allyl, undecenyl, benzyl, phenyl, tetrahydrofurfuryl, $C_2$-$C_3$alkyl substituted in the 2- or 3-position by $C_1$-$C_4$alkoxy, by dimethylamino or by diethylamino; or $R_8$ can also be hydrogen, or

is 4-morpholinyl, and, when n is 2, $R_2$ is one of the groups of the formulae (IIIa)-(IIId) in which $R_{10}$ is a direct bond, $C_1$-$C_{10}$alkylene, $C_2$-$C_8$alkylene interrupted by 1, 2 or 3 oxygen atoms or by 1 or 2>N—$R_{13}$ groups with $R_{13}$ being as defined above for $R_5$ and $R_6$; $C_2$-$C_{15}$alkylidene, phenyl-($C_1$-$C_{10}$alkylidene), cyclohexylene, cyclohexenylene, phenylene or $C_2$-$C_{14}$alkenylene, $R_{11}$ is $C_2$-$C_{10}$alkylene, $C_4$-$C_8$alkylene interrupted by 1 or 2 oxygen atoms; cyclohexylenedimethylene, methylenedicyclohexylene, isopropylidenedicyclohexylene or isopropylidenediphenylene, $R_{12}$ is as defined above for $R_{11}$ or tolylene, methylenediphenylene or a group

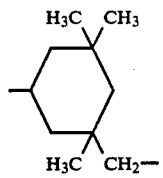

and Z is as defined above for X and Y, and, when n is 3, $R_2$ is aliphatic $C_4$-$C_7$triacyl, a group N(CH$_2$CO—)$_3$, aromatic $C_9$-$C_{10}$triacyl, or a 1,3,5-triazine-2,4,6-triyl group.

4. A method according to claim 1, in which $R_1$ is phenyl, n is 1, 2 or 3 and, when n is 1, $R_2$ is one of the groups of the formulae (IIa)-(IIc) in which $R_3$ is $C_3$-$C_{17}$alkyl, cyclohexyl, $C_2$-$C_{10}$alkenyl, 2-(3,5-di-t-butyl-4-hydroxyphenyl)-ethyl, phenyl or 3,5-di-t-butyl-4-hydroxyphenyl, $R_4$ is $C_2$-$C_{18}$alkyl, cyclohexyl, trimethylcyclohexyl, t-butylcyclohexyl or allyl, $R_5$ and $R_6$ which can be identical or different are hydrogen, $C_1$-$C_{12}$alkyl, cyclohexyl or benzyl, and, when n is 2, $R_2$ is one of the groups of the formulae (IIIa)-(IIIc) in which $R_{10}$ is a direct bond, $C_1$–$C_8$alkylene, $C_4$–$C_{13}$alkylidene, phenyl-($C_1$–$C_8$alkylidene), cyclohexylene, cyclohexenylene, phenylene or vinylene, $R_{11}$ is $C_4$–$C_8$alkylene, cyclohexylenedimethylene, isopropylidenedicyclohexylene or isopropylidenediphenylene, $R_{12}$ is as defined above for $R_{11}$ or is methylenedicyclohexylene, tolylene, methylenediphenylene or a group

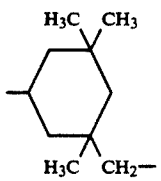

and, when n is 3, $R_2$ is aliphatic $C_5$–$C_7$triacyl, a group $N(CH_2CO\text{—})_3$ or benzenetricarbonyl.

5. A method according to claim 1, in which $R_1$ is phenyl, n is 1, 2 or 3 and, when n is 1, $R_2$ is one of the groups of the formulae (IIa)–(IIc) in which $R_3$ is $C_4$–$C_{17}$alkyl, $R_4$ is $C_4$–$C_{18}$alkyl, cyclohexyl or t-butylcyclohexyl, $R_5$ and $R_6$ which can be identical or different are $C_2$–$C_8$alkyl or cyclohexyl and $R_5$ can also be hydrogen, and, when n is 2, $R_2$ is one of the groups of the formulae (IIIa)–(IIIc) in which $R_{10}$ is $C_2$–$C_8$alkylene, $R_{11}$ is $C_4$–$C_6$alkylene and $R_{12}$ is $C_4$–$C_6$alkylene, and, when n is 3, $R_2$ is benzenetricarbonyl.

6. A method according to claim 1, wherein n is 1.

7. A method according to claim 1, wherein the synthetic thermoplastic material is a polyolefin.

8. A method according to claim 1, wherein the synthetic thermoplastic material is polyethylene or polypropylene.

9. A composition containing a polyolefin and a compound of the formula (I) according to claim 1.

10. A compound of the formula (Ia)

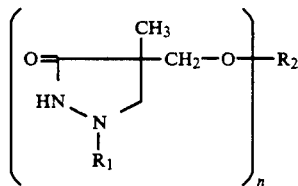

(Ia)

in which $R_1$ is phenyl unsubstituted or substituted by 1,2 or 3 radicals selected from the group consisting of $C_1$–$C_4$alkyl, $C_1$–$C_4$alkoxy and OH; n is 1, 2, 3 or 4 and, when n is 1, $R_2$ is a radical of the formula (IId)

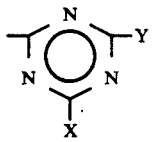

(IId)

in which X and Y which can be identical or different are a group —$OR_7$, —$SR_7$ or

where $R_7$, $R_8$ and $R_9$ which can be identical or different are hydrogen, $C_1$–$C_{18}$alkyl, $C_5$–$C_{12}$cycloalkyl unsubstituted or mono-, di- or tri-substituted by $C_1$–$C_4$alkyl; $C_3$–$C_{18}$alkenyl, $C_7$–$C_9$phenylalkyl unsubstituted or substituted on the phenyl by 1, 2 or 3 radicals selected from the group consisting of $C_1$–$C_4$alkyl and OH; phenyl unsubstituted or substituted by 1, 2 or 3 radicals selected from the group consisting of $C_1$–$C_4$alkyl, $C_1$–$C_4$alkoxy and OH; tetrahydrofurfuryl, $C_2$–$C_4$alkyl substituted in the 2-, 3- or 4-position by $C_1$–$C_8$alkoxy or by di-($C_1$–$C_4$alkyl)-amino; or

is a 5-membered to 7-membered heterocyclic group, and, when n is 2, $R_2$ is one of the radicals of the formulae (IIIb)–(IIId)

—COO—$R_{11}$—OOC—,  —CONH—$R_{12}$—NHCO—, (IIIb)  (IIIc)

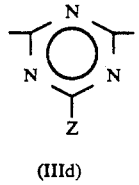

(IIId)

in which $R_{11}$ is $C_2$–$C_{12}$ alkylene, $C_4$–$C_{12}$alkylene interrupted by 1, 2 or 3 oxygen atoms; cyclohexylene, cyclohexylenedimethylene, methylenedicyclohexylene, isopropylidenedicyclohexylene, phenylene, isopropylidenediphenylene or xylylene, $R_{12}$ is as defined above for $R_{11}$ or is tolylene, methylenediphenylene or a group

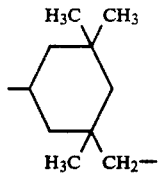

and Z is as defined above for X and Y, and, when n is 3, $R_2$ is a member selected from aliphatic $C_4$–$C_{18}$triacyl, aliphatic $C_6$–$C_{18}$triacyl containing a trisubstituted nitrogen atom; aromatic $C_9$–$C_{18}$triacyl, heterocyclic triacyl having up to 18 carbon atoms or 1,3,5-triazine-2,4,6-triyl, and, when n is 4, $R_2$ the group consisting of aliphatic $C_6$–$C_{18}$tetraacyl, aliphatic $C_{10}$–$C_{18}$tetraacyl containing 2 trisubstituted nitrogen atoms; aromatic $C_{10}$–$C_{18}$tetraacyl or cycloaliphatic $C_{10}$–$C_{22}$tetraacyl.

* * * * *